(12) United States Patent
Batzer et al.

(10) Patent No.: US 9,717,431 B2
(45) Date of Patent: Aug. 1, 2017

(54) CIRCUIT ARRANGEMENT FOR SUPPRESSING COMMON-MODE INTERFERENCE SIGNALS DURING THE MEASUREMENT OF BIOELECTRIC SIGNALS

(71) Applicants: Ulrich Batzer, Buckenhof (DE); Peter Greif, Pinzberg/Gosberg (DE); Harald Karl, Fürth (DE)

(72) Inventors: Ulrich Batzer, Buckenhof (DE); Peter Greif, Pinzberg/Gosberg (DE); Harald Karl, Fürth (DE)

(73) Assignee: Siemens Aktiengesellschaft, München (DE)

( * ) Notice: Subject to any disclaimer, the term of this patent is extended or adjusted under 35 U.S.C. 154(b) by 8 days.

(21) Appl. No.: 14/872,841

(22) Filed: Oct. 1, 2015

(65) Prior Publication Data
US 2016/0095528 A1    Apr. 7, 2016

(30) Foreign Application Priority Data
Oct. 1, 2014    (DE) .......................... 10 2014 219 943

(51) Int. Cl.
*A61B 5/00*      (2006.01)
*A61B 5/0408*    (2006.01)
(Continued)

(52) U.S. Cl.
CPC .......... *A61B 5/0408* (2013.01); *A61B 5/0428* (2013.01); *A61B 5/0809* (2013.01);
(Continued)

(58) Field of Classification Search
CPC ....... A61B 5/04; A61B 5/0402; A61B 5/0428; A61B 5/72; A61B 5/7203; A61B 5/7207; A61B 5/7225
See application file for complete search history.

(56) References Cited

U.S. PATENT DOCUMENTS 4,320,351 A * 3/1982 Brown, Jr. ................. H03F 3/68
                                                    330/260
4,512,752 A * 4/1985 Brenneman ............... F16H 7/14
                                                    474/114
(Continued)

OTHER PUBLICATIONS

German Office action for related German Application No. 10 2014 219 943.3, dated Jun. 26, 2015, with English Translation.
(Continued)

*Primary Examiner* — Allen Porter, Jr.
(74) *Attorney, Agent, or Firm* — Lempia Summerfield Katz LLC

(57) ABSTRACT

A differential voltage measuring system includes two electrodes that are connected to a patient at an input and make available a respective measurement contact at an output. A shunt resistor is connected in series with the second electrode. A first amplifier circuit has a first input for a first signal from the first electrode, a second input for a second signal from the second electrode, and an output. A second amplifier circuit has a first input that is connected in series with the shunt resistor, a second input that is connected in parallel with the shunt resistor, and an output. A first signal detection unit is provided at the output of the first amplifier circuit, and a second signal detection unit is provided at the output of the second amplifier circuit. The second signal detection unit detects the signal from the second amplifier circuit as a measurement variable.

11 Claims, 8 Drawing Sheets

(51) Int. Cl.
*A61B 5/08* (2006.01)
*G01R 19/10* (2006.01)
*A61B 5/0428* (2006.01)

(52) U.S. Cl.
CPC .......... *A61B 5/7203* (2013.01); *A61B 5/7225* (2013.01); *G01R 19/10* (2013.01)

(56) References Cited

U.S. PATENT DOCUMENTS

| | | | |
|---|---|---|---|
| 6,275,102 B1* | 8/2001 | Muza | H03F 1/34 |
| | | | 330/69 |
| 6,496,721 B1* | 12/2002 | Yonce | A61B 5/0428 |
| | | | 600/509 |
| 6,693,486 B1* | 2/2004 | Brockhaus | G01F 1/60 |
| | | | 330/124 R |
| 6,950,694 B2 | 9/2005 | Yonce | |
| 7,420,413 B2* | 9/2008 | Tsurumi | H03F 1/342 |
| | | | 330/295 |
| 7,587,239 B1* | 9/2009 | Kroll | A61N 1/368 |
| | | | 128/902 |
| 7,863,977 B1* | 1/2011 | Xiang | A61B 5/0428 |
| | | | 330/124 R |
| 8,519,792 B2 | 8/2013 | Chang et al. | |
| 2003/0073916 A1 | 4/2003 | Yonce | |
| 2010/0007413 A1* | 1/2010 | Herleikson | A61B 5/0424 |
| | | | 330/124 R |
| 2011/0204971 A1 | 8/2011 | Chang et al. | |
| 2014/0257119 A1* | 9/2014 | LeMay | A61B 5/6844 |
| | | | 600/509 |

OTHER PUBLICATIONS

M. Yelderman, B. Widrow, J. M. Cioffi, E. Hesler and J. A Leddy "ECG enhancement by adaptive cancellation of electrosurgical interference," IEEE Trans. Biomed. Eng., vol. BME-30, pp. 392-398 1983, http://www-isl.stanford.edu/~widrow/papers/j1983ecgenhancement.pdf; 1983.

Texas Instruments, ADS129x manual, Jan. 2014, http://www.ti.com/lit/ds/symlink/ads1298.pdf, 2014.

* cited by examiner

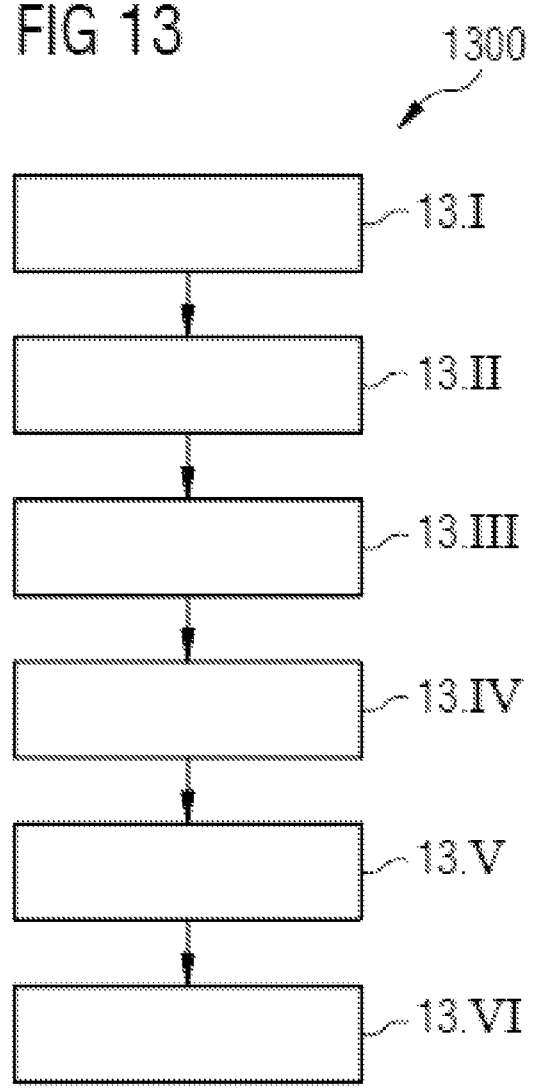

CIRCUIT ARRANGEMENT FOR SUPPRESSING COMMON-MODE INTERFERENCE SIGNALS DURING THE MEASUREMENT OF BIOELECTRIC SIGNALS

This application claims the benefit of DE 10 2014 219 943.3, filed on Oct. 1, 2014, which is hereby incorporated by reference in its entirety.

BACKGROUND

The present embodiments relate to a differential voltage measuring system, a differential voltage measuring system for measuring a respiration movement, a differential voltage measuring system including a driver circuit for the right leg, and a method for differentially measuring voltages.

During the measurement of bioelectric signals (e.g., of ECG signals), common-mode interference signals (e.g., interference as a result of common-mode signals) occur as a result of non-ideal measurement inputs of an ECG measuring arrangement. The signals arise, for example, from the power supply frequency at 50 Hz. Common-mode interference signals occur if non-identical conditions such as different impedances and capacitances occur at the two measurement inputs during the differential ECG signal measurement. One example of a conventional measuring arrangement for measuring an electrocardiogram is shown in FIG. 1. In fact, common-mode signals (e.g., interference signals) are not concomitantly amplified during the differential measurement, and so the common-mode signals are suppressed. However, the different impedances of the inputs of the ECG measuring arrangement have the effect that different input signals caused by the same interference signal are present at the two inputs of an amplifier circuit of an ECG measuring arrangement, such that the interference signal is amplified together with the actual measurement signal. These common-mode interference signals are very strong in the application on a patient (e.g., a human being or an animal), since the electrode contacts on the skin of the patient have a greatly varying quality factor without complex preparation. An electrode contact on the patient may have impedances of between 10 kohms and several megohms and likewise greatly varying capacitances. As a result, the difference between the impedances and capacitances at two measurement inputs is also in the range of up to several megohms. One example of an ECG signal subjected to common-mode interference by an impedance difference of 500 kohms is shown in FIG. 2. In some instances, the impedance differences at the inputs of the ECG measuring arrangement are even higher, such that an evaluation of the ECG signal hardly appears to be possible any longer.

By contrast, the total sum of the impedances of the electrode contacts is hardly of importance any longer on account of progress in the art with input impedances of from hundreds of megohms to several gigaohms; it is completely irrelevant to the common-mode interference signals.

Conventionally, there are various procedures for suppressing common-mode noise.

One possible procedure includes the measurement of a common-mode current and an adaptive filtering adapted to the measured common-mode current. In this case, the common-mode current is measured separately with the aid of two separate electrodes. The two electrodes are arranged at a distance from the heart and in spatial proximity to one another, such that only common-mode signals are measured by the two electrodes. However, the common-mode measurement electrodes and the ECG measurement electrodes have different impedances, such that the measured common-mode signal may not simply be subtracted from the differential signal measured at the ECG measurement electrodes. Therefore, with the aid of an adaptive filter, the different transfer function of the electrodes is simulated, and the common-mode interference signal is filtered out of the differential measurement signal present at the ECG measurement electrodes. However, this procedure functions only during the suppression of non-correlated common-mode signals. If correlated common-mode signals occur, filtering the common-mode signals also leads to filtering out or attenuation of the measurement signals or useful signals.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a simpler and universally usable ECG measuring circuit that is suitable for correlated common-mode and useful signals and in which the interference as a result of common-mode signals is effectively suppressed is provided.

The differential voltage measuring system according to one or more of the present embodiments includes two electrodes that are connected to a patient at an input and make available a respective measurement contact at an output. Hereinafter, a differential voltage measuring system may be a measuring system that measures voltage differences.

The differential voltage measuring system according to one or more of the present embodiments further includes a shunt resistor connected in series with the second electrode. The shunt resistor serves for measuring the common-mode component of the measurement signal or differential signal present at the two electrodes.

The differential voltage measuring system also includes a first amplifier circuit having a first input for a first signal from the first electrode and a second input for a second signal from the second electrode and an output. The conduction path includes the first electrode as far as the first input of the first amplifier circuit is also designated hereinafter as first measurement path. Via the first measurement path, the first measurement signal present at the first electrode is fed to the first input of the first amplifier circuit. The conduction path including the second electrode and the shunt resistor as far as the second input of the first amplifier circuit is also designated hereinafter as second measurement path. Via the second measurement path, the second measurement signal present at the second electrode is fed to the second input of the first amplifier circuit. The first amplifier circuit is used for measuring a differential signal resulting from the signals present at the first electrode and the second electrode.

The differential signal also has common-mode components that result on account of a different impedance of the first measurement path and of the second measurement path. For determining the common-mode component, the differential voltage measuring system includes a second amplifier circuit having a first input, a second input, and an output. The first input of the second amplifier circuit is connected between the shunt resistor and the second input of the first amplifier circuit, and the second input of the second amplifier circuit is connected between the second electrode and the shunt resistor. The second amplifier circuit measures a voltage drop at the shunt resistor and thus a variable proportional to the current intensity of the common-mode current or common-mode signal.

The differential voltage measuring system also includes a first signal detection unit at the output of the first amplifier circuit for detecting the differential signal measured by the first amplifier circuit. A second signal detection unit at the output of the second amplifier circuit detects the signal from the second amplifier circuit as a voltage drop at the shunt resistor or, given a known value of the resistance of the shunt resistor, as a measurement variable of the current intensity of the common-mode current.

If the impedance values of the measurement paths are known, for example, then the common-mode component of the measured differential signal may be deduced from the common-mode current determined, and the correct measurement signal or useful signal may be determined, for example, by subtraction of the common-mode component from the differential signal.

The differential voltage measuring system according to one or more of the present embodiments for measuring a respiration movement includes a plurality of measurement paths each including an electrode for detecting a signal present at the respective electrode. The differential voltage measuring system also includes at least one amplifier circuit having a first input that is electrically connected to a first electrode, and a second input that is electrically connected to a second electrode. The amplifier circuit determines a differential signal from the signals present at the first and second electrodes. The differential voltage measuring system according to one or more the present embodiments includes a signal detection circuit configured to detect a differential signal determined by the at least one amplifier circuit. The differential voltage measuring system also includes an additional amplifier circuit, both inputs of which are respectively coupled via a capacitance to one of the electrodes. The differential voltage measuring system also includes at least one additional current path that is provided with an additional impedance, is coupled to one of the electrodes, and is dimensioned such that the transfer functions of the individual measurement paths assigned to the individual electrodes are matched to one another.

In other words, the symmetry of the measurement paths is established by the additional impedance, such that an interference signal that may occur as a common-mode current on account of the different impedances of the measurement paths does not arise even upon the occurrence of strong voltage pulses.

The differential voltage measuring system according to one or more of the present embodiments including a driver circuit for the right leg includes two electrodes that are connected to a patient at the input and make available a respective measurement contact at the output. The differential voltage measuring system also includes an amplifier circuit having a first input for a first signal from the first electrode, a second input for a second signal from the second electrode, and an output. A signal detection unit is connected to the output of the first amplifier circuit.

The differential voltage measuring system according to one or more of the present embodiments also includes a further contact for generating a reference signal on the body of the patient. By way of example, the further contact is connected to the right leg of the patient. This is also designated as RLD path. The differential voltage measuring system according to one or more of the present embodiments also includes a control unit that reads the signals from the signal detection unit and drives the further contact such that a reference signal corresponding to a measured common-mode voltage is generated on the body of the patient.

The differential voltage measuring system according to one or more of the present embodiments includes a plurality of protective resistors exclusively between the first electrode and the first input of the amplifier circuit and the second electrode and the second input of the amplifier circuit, such that the impedance of the further contact is minimized. The protective resistors serve to limit patient auxiliary currents. A patient auxiliary current is a current that flows during use as intended in the patient between any patient terminal and all other patient terminals, and is not intended to produce a physiological effect. This type of currents is not to exceed specific defined values in order not to endanger the patient. Conventionally, the protective resistors are distributed uniformly over the measurement paths and the RLD path. However, this uniform distribution is disadvantageous for a measurement of ECG signals since the common-mode component of the measurement signal that is undesired during the measurement is dependent on the currents flowing through the measurement paths. The currents flowing through the measurement paths are to be as small as possible, while the current via the RLD path is to be as large as possible. In order to achieve this, according to one or more of the present embodiments, the protective resistors are distributed only among the measurement paths, such that the resistance thereof is increased in comparison with conventional measuring circuits, and the resistance value of the electrical resistance of the RLD path is reduced in comparison with conventional measuring circuits. Interference components of the measurement signal during the measurement are reduced in this way. The transfer of the resistances to the measurement paths does not change anything about the sums of the resistance values or the total resistance values between two arbitrary poles or patient contacts, such that nothing changes with regard to the limitation of the patient auxiliary currents.

In the method according to one or more of the present embodiments for differentially measuring voltages, a first signal is detected with a first electrode, and a second signal is detected with a second electrode. The first electrode and the second electrode are connected to a patient at the input and make available a respective measurement contact at the output.

A common-mode current is measured at a shunt resistor connected to the second electrode, and, a corrected value of the differential voltage signal is determined based on the measurement values determined. As already mentioned, this may be done the most easily given known impedance values of the measurement paths. If these values are not known and if the common-mode signal and useful signal are not correlated, then an adaptive filter may also be used based on the common-mode current determined. The common-mode component is filtered out of the measurement signal by the adaptive filter.

The method according to one or more of the present embodiments for differentially measuring voltages may also be developed analogously to the device of one or more of the present embodiments.

In one configuration of the differential voltage measuring system, the differential voltage measuring system includes an adaptive filter between one of the two electrodes and one of the two inputs of the first amplifier circuit. The filter is set such that the common-mode current is suppressed. In other words, with the aid of an adaptive filter, the different transfer function of the electrodes is simulated, and the common-mode interference signal is filtered out of the differential measurement signal present at the ECG measurement electrodes or determined by the first amplifier circuit. As already mentioned, this variant is particularly effective if the common-mode signal and the useful signal are not correlated.

Alternatively or additionally, the differential voltage measuring system according to one or more of the present embodiments includes a first unit and a second unit for DC current generation, AC voltage generation, or AC current generation at the two inputs of the first amplifier circuit. The differential voltage measuring system also includes an evaluation unit configured to determine the transfer function of the first electrode and of the second electrode based on the voltage values measured at the two inputs. This variant of the differential voltage measuring system is particularly effective if the common-mode signal and the useful signal are correlated. In this case, with the use of an adaptive filter, the useful signal may also be attenuated. By contrast, in the case of this alternative variant, the impedance values of the measurement paths are determined by the DC voltage, AC voltage, or AC current generation. This results in the transfer functions of the measurement paths, such that the voltage of the common-mode signal or common-mode interference signal may be determined, for example, from the transfer functions for the measurement path provided with a shunt resistor and the common-mode current measured with the shunt resistor. The correct or corrected measurement value then results from the difference between the voltage of the measurement signal and the voltage value of the common-mode interference signal.

In one configuration, the differential voltage measuring system includes a control unit for controlling the first and second units for DC voltage, AC voltage, or AC current generation at the two inputs of the first amplifier circuit. In this case, the control unit is configured to drive the two units such that AC current signals having a varying frequency are generated at the first electrode and the second electrode. The impression of suitable AC currents is suitable if temporally variable interference occurs. In this case, the most effective procedure is if the frequencies of the test signals include the expected frequencies of the interference.

In one alternative configuration of the differential voltage measuring system, the control unit is configured to drive the first unit and the second unit for DC current generation, AC voltage generation, or AC current generation such that AC current signals having an impulse or step-response function are generated at the first electrode and the second electrode.

In one variant of the differential voltage measuring system, the evaluation device is configured to determine, based on the detected current intensity of the common-mode current and the determined transfer function, the common-mode voltage generated by the common-mode current at the shunt resistor and to subtract the common-mode voltage from the measurement signal or differential signal detected by the first signal detection unit. This manner of determining the undisturbed measurement signal may be provided upon the occurrence of interference signals that are correlated with the useful signal.

The differential voltage measuring system according to one or more of the present embodiments may also include a plurality of measurement electrodes corresponding to the first electrode that are connected to a patient at the input and make available a respective measurement contact at the output. The use of a larger number of measurement electrodes yields an improved measurement accuracy, in principle. In this case, the arrangement may be fashioned particularly compactly and cost-effectively if one or a plurality of multiplexers connected upstream are used, by which further measurement contacts may be connected to the first and second inputs or signal input of the amplifier circuit.

In one configuration of the differential voltage measuring system having a particularly good precision in the detection of useful signal and interference signal, the arrangement also includes for each electrode a measurement path for measuring common-mode currents. The measurement path is provided with a shunt resistor and may be connected to the respective electrode. In other words, in the case of this arrangement, the shunt resistor is not integrated in the measurement path for the useful signal (e.g., the second measurement path), but rather in a separate measurement path that branches off therefrom and may be connected in during a measurement of the common-mode currents, but is not connected in during the actual measurement of the useful signal, such that the shunt resistor does not cause any additional measurement inaccuracy, for example, as a result of thermal noise.

In addition, the differential voltage measuring system may have a further contact for generating a signal that may be regulated to the common-mode voltage determined at the shunt resistor. In the case of this variant of the differential voltage measuring system, the RLD path is not driven with a measured average voltage of the signals present at the measurement paths. Rather, the common-mode voltage determined at the shunt resistor is used as reference signal, which results in an improved compensation of the interference signals in comparison with a conventional arrangement with RLD path.

In the case of an alternative variant of the differential voltage measuring system, the shunt resistor is arranged in a third current path that branches off from the current path formed by the second electrode and the second input of the first amplifier at the output of the second electrode. Interference of the useful signal as a result of thermal noise of the shunt resistor is avoided in this way. In order that the impedance or the transfer function of the third current path corresponds to the transfer function of the second current path, in this variant, the third current path also includes a regulatable impedance connected between the shunt resistor and ground.

BRIEF DESCRIPTION OF THE DRAWINGS

The figures are generally not to scale.

FIG. 13 shows a flow diagram illustrating a method for differentially measuring voltages in accordance with one exemplary embodiment.

DETAILED DESCRIPTION

Figure 1:
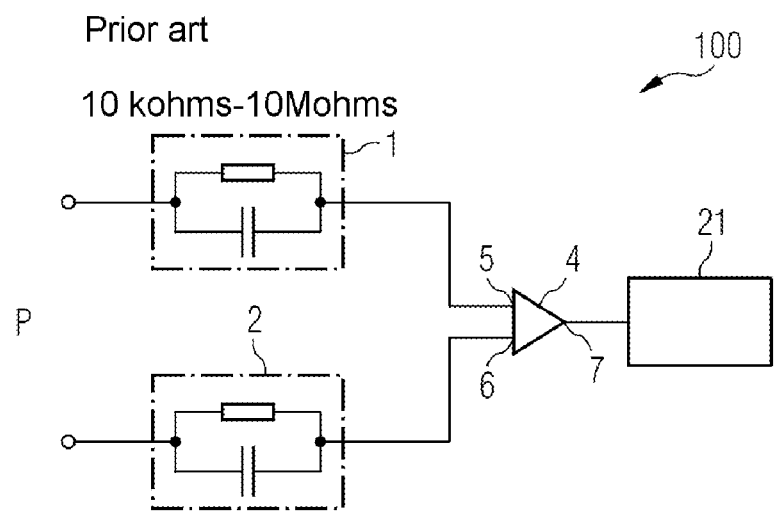
FIG. 1 shows a block diagram of a conventional ECG measuring arrangement.

FIG. 1 shows a conventional circuit arrangement 100 for measuring an electrocardiogram (ECG) of a patient P. The circuit arrangement 100 includes a first electrode 1 and a second electrode 2. The first electrode 1 and the second electrode 2 are in contact with the patient P such that a heart current may flow via the electrodes to a differential amplifier 4. The differential amplifier 4 includes a first input 5, a second input 6, and an output 7. The first input 5 is electrically connected to the first electrode 1, and the second input 6 is electrically connected to the second electrode 2. The output signal of the amplifier 4 is communicated to a signal detection unit 21, which detects the signal amplified by the amplifier 4. The two electrodes 1 and 2 are symbolized by an RC element illustrating the impedance values of the first measurement path and of the second measurement path. In this case, the first measurement path runs from the contact of the first electrode 1 with the patient P via the first electrode 1 to the first input 5 of the amplifier 4, and the second measurement path runs from the contact of the second electrode 2 with the patient via the second electrode 2 to the second input 6 of the amplifier 4.

Figure 2:
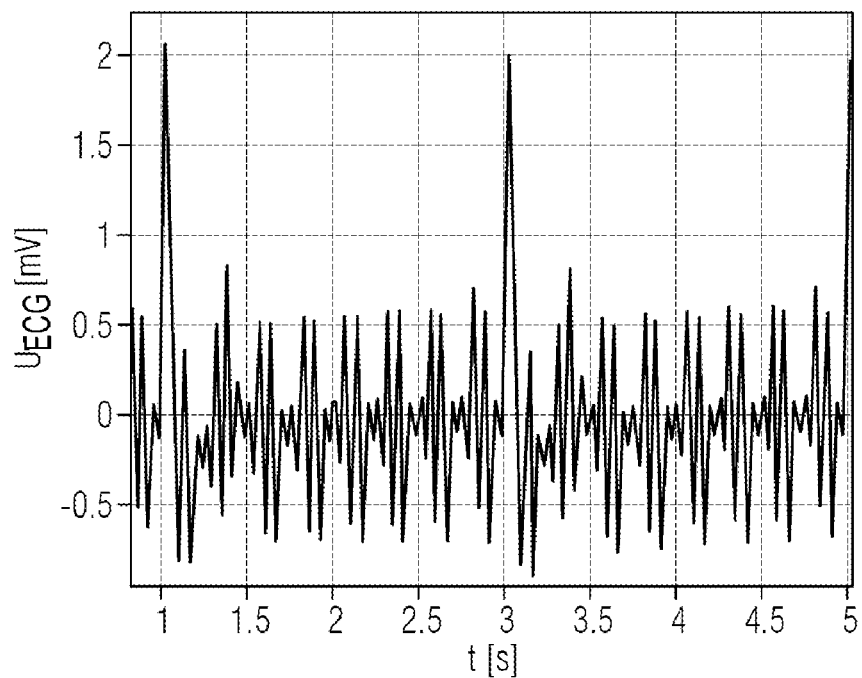
FIG. 2 shows a graph showing an ECG with interference signals superimposed thereon.

One example of an ECG signal subjected to common-mode interference as a result of an impedance difference of 500 kohms is shown in FIG. 2. The associated test set-up corresponds to the set-up in FIG. 1. In the graph shown, the amplitude $U_{ECG}$ of the ECG signal in mV is plotted against time t in seconds. The amplitude of the interference sources is approximately 1.3 mV in the example with an impedance difference of 500 kohms. In this example, there is a strong ECG signal having an amplitude of more than 2 mV, but there are also patients having an amplitude of only 0.1 mV, which would completely vanish in these interference sources. In the case of larger impedance differences, the amplitude of the common-mode interference signals rises further and may also reach multiples of the representation shown.

Figure 3:
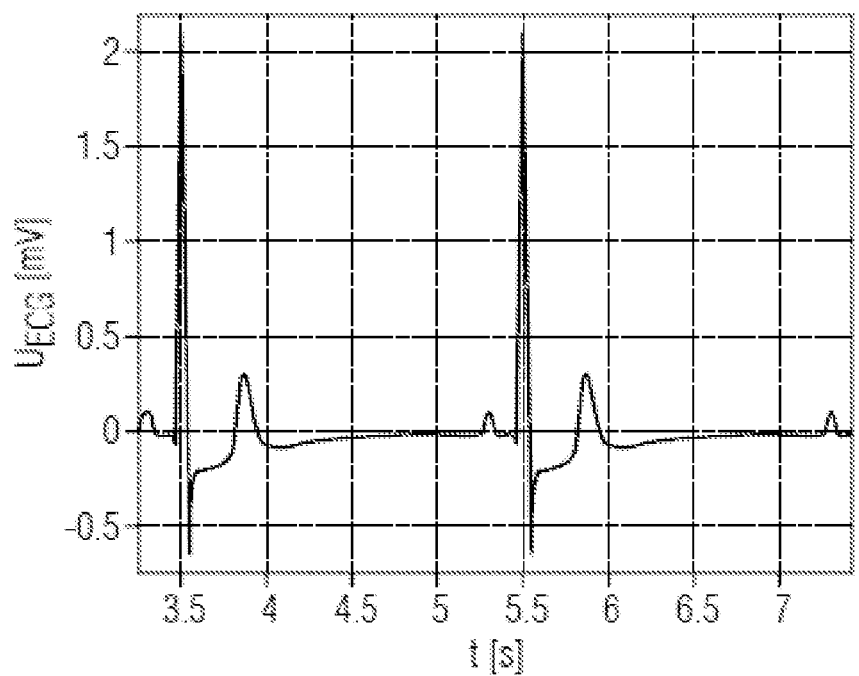
FIG. 3 shows a graph showing an undisturbed ECG detected by a measuring circuit in accordance with an exemplary embodiment.

One example for two heart beats of an undisturbed ECG signal is shown in FIG. 3. In the graph in FIG. 3, an ECG voltage $U_{ECG}$ in mV is plotted against time t in seconds. The characteristic features of an ECG curve such as the R-wave and the s-wave, for example, may readily be discerned in the graph in FIG. 3. However, such an undisturbed ECG signal may hardly be achieved with the arrangement in FIG. 1 since usually the input resistances of the measuring circuit 100 are not identical and interference signals (e.g., common-mode interference signals) thus occur.

Figure 4:
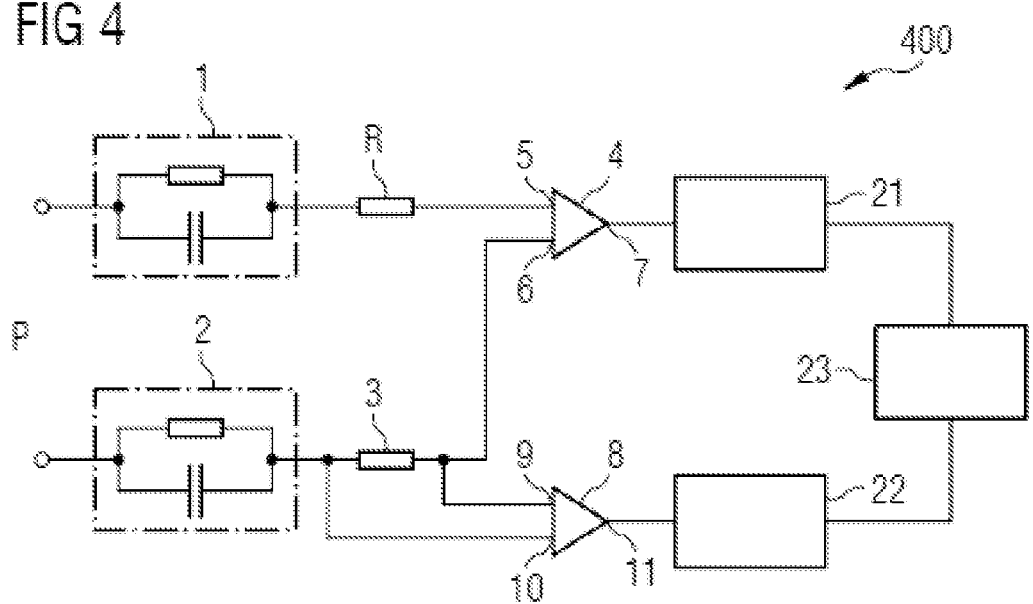
FIG. 4 shows a circuit arrangement in accordance with a first exemplary embodiment.

FIG. 4 illustrates a circuit arrangement 400 for differential measurements of ECG signals in accordance with a first exemplary embodiment.

A first electrode 1 is connected by an input to a patient P. The first electrode 1 is part of a first measurement path including the first electrode 1 and a resistor R. A second electrode 2 is also electrically connected by its input to the patient P. The second electrode 2 is connected by an output to a shunt resistor 3 and with the shunt resistor 3 forms a second measurement path.

A first amplifier circuit 4 includes a first input 5 and a second input 6 and an output 7. The first amplifier circuit 4 is connected by a first input 5 to the first electrode 1 via the resistor R. The first amplifier circuit 4 is electrically connected by a second input 6 via the shunt resistor 3 to the second electrode 2. The output 7 of the first amplifier circuit 4 is connected to an input of a signal detection unit 21. An output of the signal detection unit 21 is connected to an input of an evaluation unit 23.

A second amplifier circuit 8 includes a first input 9 and a second input 10. The first input 9 of the second amplifier circuit 8 is connected between the shunt resistor 3 and the second input 6 of the first amplifier circuit 4, and the second input 10 of the second amplifier circuit 8 is connected between the second electrode 2 and the shunt resistor 3. The second amplifier circuit 8 is electrically connected by an output 11 to a second signal detection unit 22.

While the first amplifier circuit 4 serves for detecting the measurement signals (e.g., heart currents of the patient) and forwards a signal corresponding to the difference between the signals detected by the first electrode 1 and the second electrode 2 to the first signal detection unit 21, the signal possibly still, however, having common-mode components, the second amplifier circuit 8 serves to determine a voltage drop at the shunt resistor 3 that is proportional to the common-mode current flowing in the second measurement path, and to forward the voltage drop to the second signal detection unit 22. The evaluation unit 23 may include an adaptive filter, for example, that is set in a manner dependent on the signal detected by the second signal detection unit 22 and filters the signal detected by the first signal detection unit 21 such that the common-mode component of the measurement signal detected by the first signal detection unit 21 is suppressed.

Alternatively, an arrangement constructed analogously to the measuring circuit in FIG. 4 may have a multi-channel set-up. A multiplex circuit may also be provided in the case of a multi-channel measuring arrangement. The circuit is fashioned significantly more compactly for the same number of measurement paths.

Figure 5:
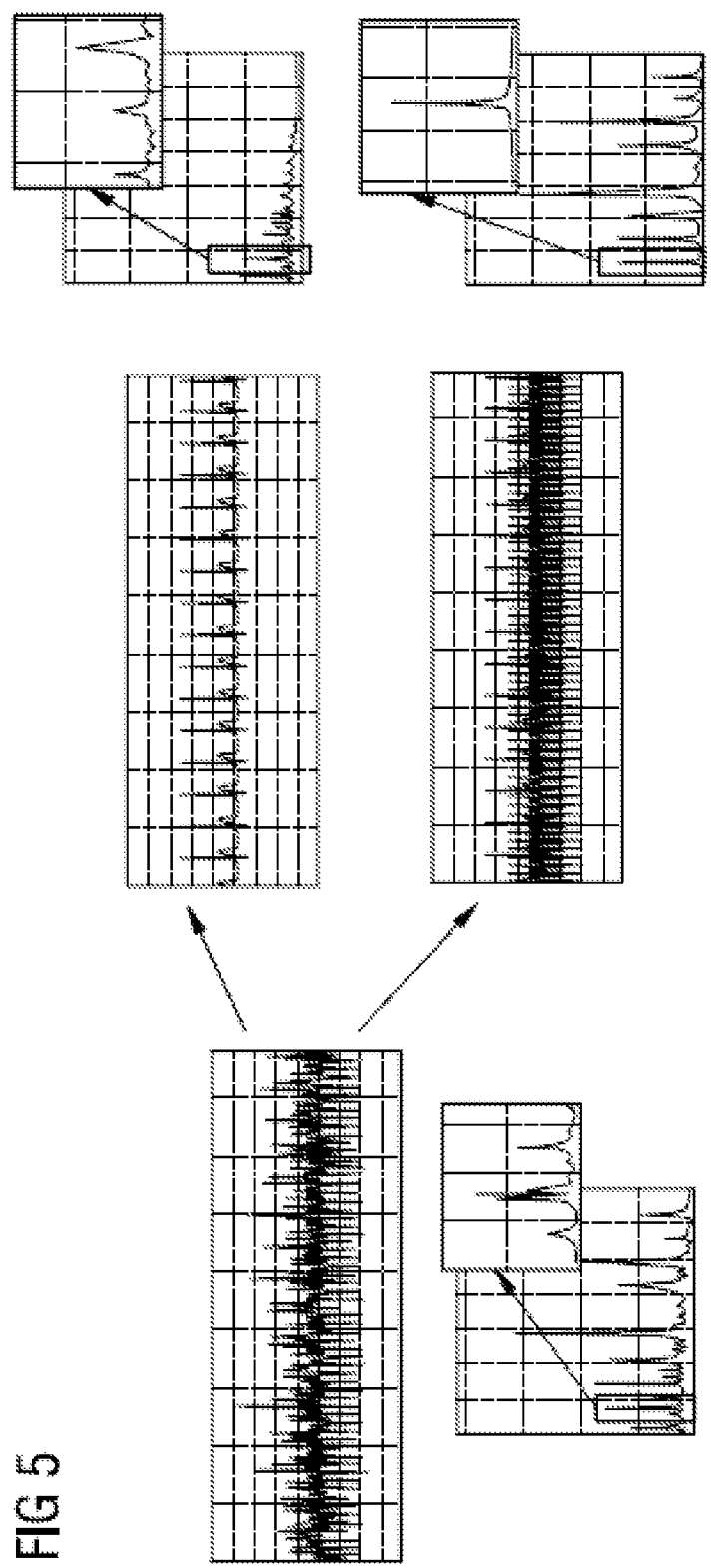
FIG. 5 shows a graph of an ECG signal beset by a correlated interference signal.

FIG. 5 shows on the left-hand side a graph of an ECG signal beset by an interference signal correlated with the measurement signal. In this case, signal amplitudes are respectively plotted against time. The interference signal results from the rotation in a CT arrangement in this case. The separation between interference signal and useful signal is less than 0.1 Hz. An enlarged excerpt from the ECG signal illustrates the superimposition of interference signal and useful signal once again in detail. The useful signal (e.g., the peak having the larger amplitude in the center of the enlarged illustration of the ECG signal) occurs practically at the same time as the interference signal (e.g., the higher-frequency signal having a smaller amplitude). Such an interference signal would no longer be able to be filtered out by a conventional arrangement since the useful signal would also be lost in the process. However, the useful signal may be effectively separated from the interference signal by the measuring circuit according to one or more of the present embodiments, such that the signal illustrated at the top on the right-hand side of FIG. 5 may be separated from the interference signal illustrated at the bottom at the right-hand side of FIG. 5. Both the filtered signal at the top right and the interference signal at the bottom left in FIG. 5 are also illustrated in enlarged views in order to be able to better discern details of the signals.

Figure 6:
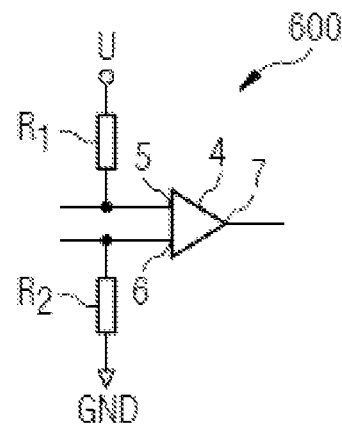
FIG. 6 shows a circuit arrangement for currentless differential resistance measurement.

FIG. 6 shows an excerpt from a measuring circuit in accordance with one exemplary embodiment. The measuring circuit is suitable for the suppression of common-mode signals correlated with the measurement signal. The arrangement 600 is based on a voltage-based differential resistance measuring method. An active measurement of the impedance of the measurement paths is realized by the measuring circuit 600 shown in FIG. 6. An additional voltage U is applied to the first input 5 of an amplifier circuit 4 via a first resistor $R_1$. The second input 6 of the amplifier circuit 4 is connected to ground GND via a second resistor $R_2$. A differential voltage is measured at the output 7 of the amplifier circuit. The impedance value of the first patient contact or of the associated first measurement path results from the differential voltage. During the measurement of the impedance of the second patient contact or of the second measurement path, the arrangement is to be correspondingly changed. In other words, the additional voltage U is applied to the second measurement path, which is electrically connected to the second input 6, and the first input 5 is connected to ground GND via a resistor. A control unit (not shown) serves for driving the measuring circuit with a voltage U and for defining the intensity and waveform of the voltage U. Based on the active determination of the impedances of the measurement paths, the voltage drop generated by the common-mode current may be determined at the shunt resistor and be subtracted from the useful signal. This computation operation may be performed, for example, by the evaluation unit 23 shown in FIG. 4. The parts of the measuring circuit 500 that are not shown may be embodied in accordance with the other exemplary embodiments illustrated.

Figure 7:
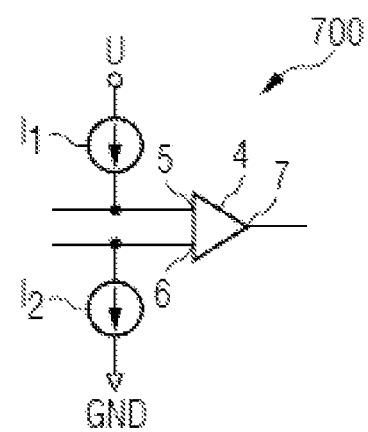
FIG. 7 shows a circuit arrangement for differential resistance measurement with the aid of current sources.

FIG. 7 schematically shows a measuring circuit 700 based on an alternative active differential resistance measuring method. In this case, the differential resistance measuring method is current-based. In the case of this procedure, an additional regulatable current source $I_1$ is connected to the first input 5 of the amplifier circuit 4 or the first measurement path. A second current source $I_2$ is connected between the second input 6 and ground GND. In this method, too, the measurement paths are actively occupied by an interference signal (e.g., a defined current), from which the impedances of the individual measurement paths are determined with the aid of the amplifier circuit 4. The parts of the alternative active measuring circuit 700 that are not shown may be embodied in accordance with the other exemplary embodiments illustrated.

Figure 8:
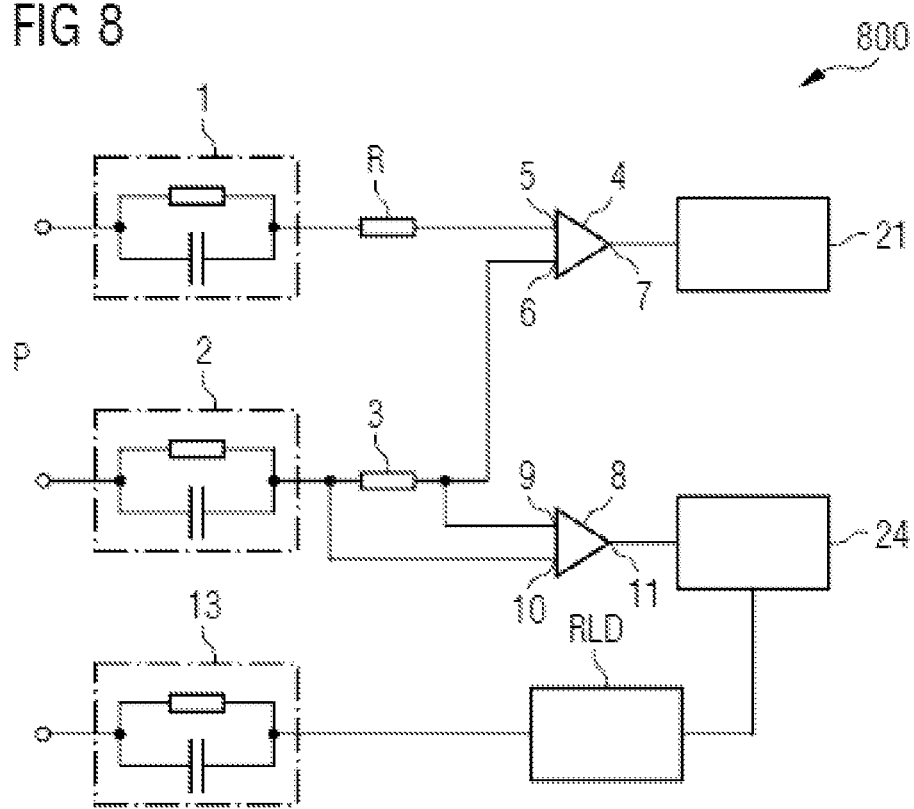
FIG. 8 shows a circuit arrangement for differential resistance measurement with a driver circuit for the right leg in accordance with one exemplary embodiment.

FIG. 8 shows a measuring circuit 800 for measuring ECG signals with an additional RLD electrode 13, which is part of an RLD path. With the exception of the additional RLD path, the circuit arrangement in FIG. 8 is constructed in a similar manner to the circuit arrangement in FIG. 4.

The circuit arrangement 800 includes a first electrode 1 that is connected by an input to a patient P. The first electrode 1 is part of a first measurement path including the first electrode 1 and a resistor R. A second electrode 2 is likewise electrically connected by an input to the patient P. The second electrode 2 is connected by an output to a shunt resistor 3 and with the shunt resistor 3, forms a second measurement path.

A first amplifier circuit 4 includes a first input 5 and a second input 6 and an output 7. The first amplifier circuit 4 is connected by a first input 5 to the first electrode 1 via the resistor R. The first amplifier circuit 4 is electrically connected by a second input 6 via the shunt resistor 3 to the second electrode 2. The output 7 of the first amplifier circuit 4 is connected to the input of a signal detection unit 21.

A second amplifier circuit 8 includes a first input 9 and a second input 10. The first input 9 of the second amplifier circuit 8 is connected between the shunt resistor 3 and the second input 6 of the first amplifier circuit 4, and the second input 10 of the second amplifier circuit 8 is connected between the second electrode 2 and the shunt resistor 3. The second amplifier circuit 8 is electrically connected by an output 11 to a control unit 24.

The additional patient contact (e.g., right leg drive (driver circuit for the right leg) or neutral electrode) provides for the potential equalization between the measuring circuit and the patient P. The RLD path includes a driver circuit RLD for the right leg. The driver circuit RLD is driven by the control unit 24 such that a reference potential is applied to the leg of the patient via the RLD electrode 13. The reference potential then results from the voltage drop measured at the shunt resistor 3 or the common-mode voltage determined therefrom. In this way, the reference potential may be fixed at the common-mode voltage more exactly than is the case, for example, in a conventional arrangement in which the reference potential is determined, for example, as a mean value from the signals present at the individual measurement paths.

Figure 9:
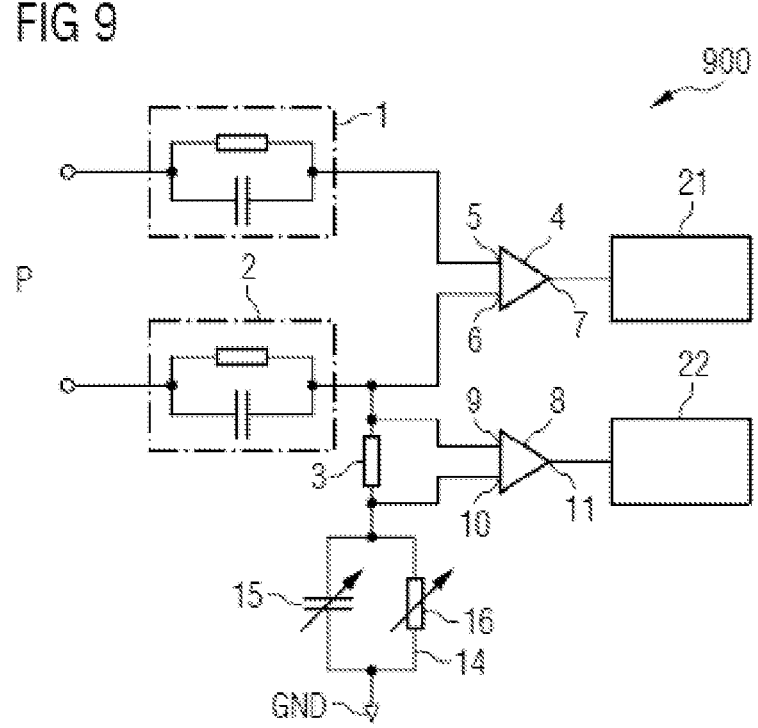
FIG. 9 shows a circuit arrangement with a separate current path for measuring the impedance of the measurement paths in accordance with one exemplary embodiment.

FIG. 9 shows a circuit arrangement 900 with a shunt resistor 3. In this embodiment, the shunt resistor 3 is arranged in an additional measurement path separated from the second measurement path or branching off therefrom. In the same way as in the circuit arrangements in FIGS. 4 and 7, a potential dropped across the shunt resistor 3 is measured by a second amplifier circuit 8 and forwarded to a signal detection unit 22. Since, in the embodiment shown in FIG. 9, the shunt resistor 3 is not situated in the second measurement path, the measurement signals detected via the first amplifier circuit 4 are also not influenced by the shunt resistor as a result of thermal noise. The additional measurement path for measuring the common-mode voltage also includes a regulatable impedance 14 having a regulatable capacitance 15 and a regulatable ohmic resistance 16. The regulatable impedance 14 may be set, for example, such that the additional measurement path for measuring the common-mode voltage has properties identical to properties of the second measurement path. Alternatively, the regulatable impedance may also be set such that a higher current flow is achieved on the additional measurement path, which contributes to an improved suppression of common-mode interference signals on the first and second measurement paths.

Figure 10:
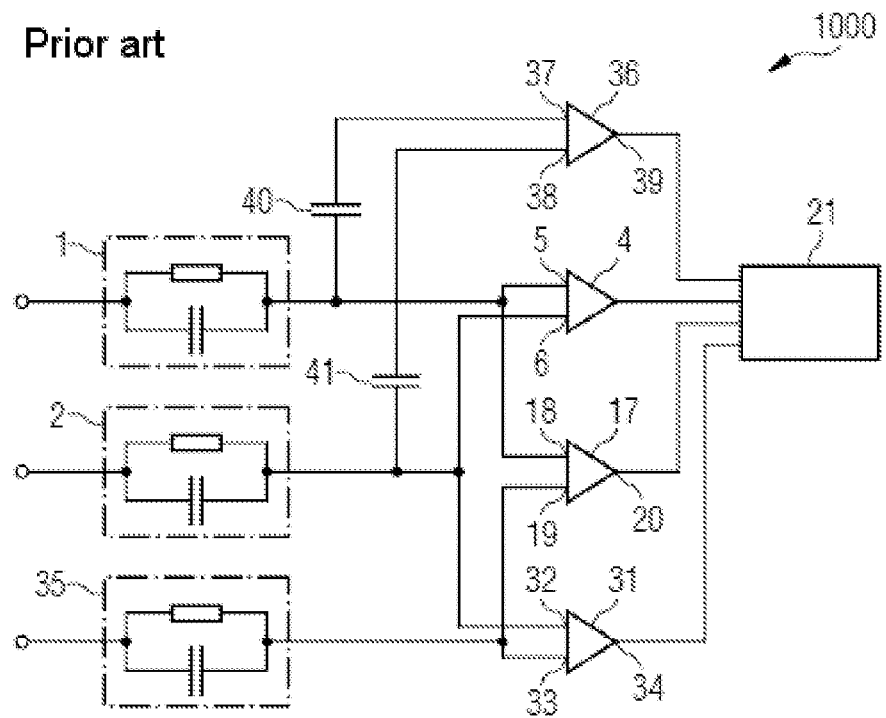
FIG. 10 shows a circuit arrangement with an ESD protective circuit in accordance with the prior art.

FIG. 10 illustrates a conventional ECG measuring circuit 1000 used for recognizing respiration and for triggering an imaging device (e.g., a CT apparatus or an MRI apparatus).

The ECG measuring circuit includes a first electrode 1, which is arranged on the right arm of a patient P, a second electrode 2, which is arranged on the left arm of a patient P, and a third electrode 35, which is in contact with the left foot of the patient P. The signals present at the electrodes 1, 2, 35 are detected differentially with the aid of amplifier circuits 4, 17 and 31 at the inputs 5, 6, 18, 19, 32 and 33 in the manner already known and are forwarded to a signal detection unit 21 via outputs 7, 20 and 34.

A separate path for recognizing respiration is additionally installed, which includes an amplifier circuit 36 having two inputs 37 and 38 and an output 39. The two inputs 37, 38 are capacitively connected to the first electrode 1 and the second electrode 2, respectively, and the output 39 is electrically connected to the signal detection unit 21. The capacitive connections are symbolized in FIG. 9 with the aid of capacitors 40, 41 connected between the first electrode 1 and the first input of the amplifier circuit of the separate path for recognizing respiration and respectively between the second electrode 2 and the second input 38 of the amplifier circuit of the separate measurement path for recognizing respiration.

On account of the additional separate measurement path, the transfer functions of the measurement paths corresponding to the first electrode 1 at the right arm of the patient and to the second electrode 2 at the left arm of the patient are not identical to the transfer function of the measurement path corresponding to the third electrode 35 at the left foot. This asymmetry is conventionally minimized by a suitable dimensioning of the capacitances 40, 41, which has the effect that given the presence of regular useful signals having an amplitude in the range of <10 mV and also common-mode interference signals having a signal amplitude in the range of <5 V, a minimal difference between the transfer functions has no effect. However, there is the risk of interference by an ESD pulse that, even with the use of an ESD protective circuitry, has a very large amplitude of up to 100 V and therefore, in the case of even only slightly asymmetrical lines having a minimal difference with regard to the transfer function, leads to a strong interference signal during the differential measurement of the signals, characterizing the respiration movement, of the first electrode 1 at the right arm and of the second electrode 2 at the left arm.

Figure 11:
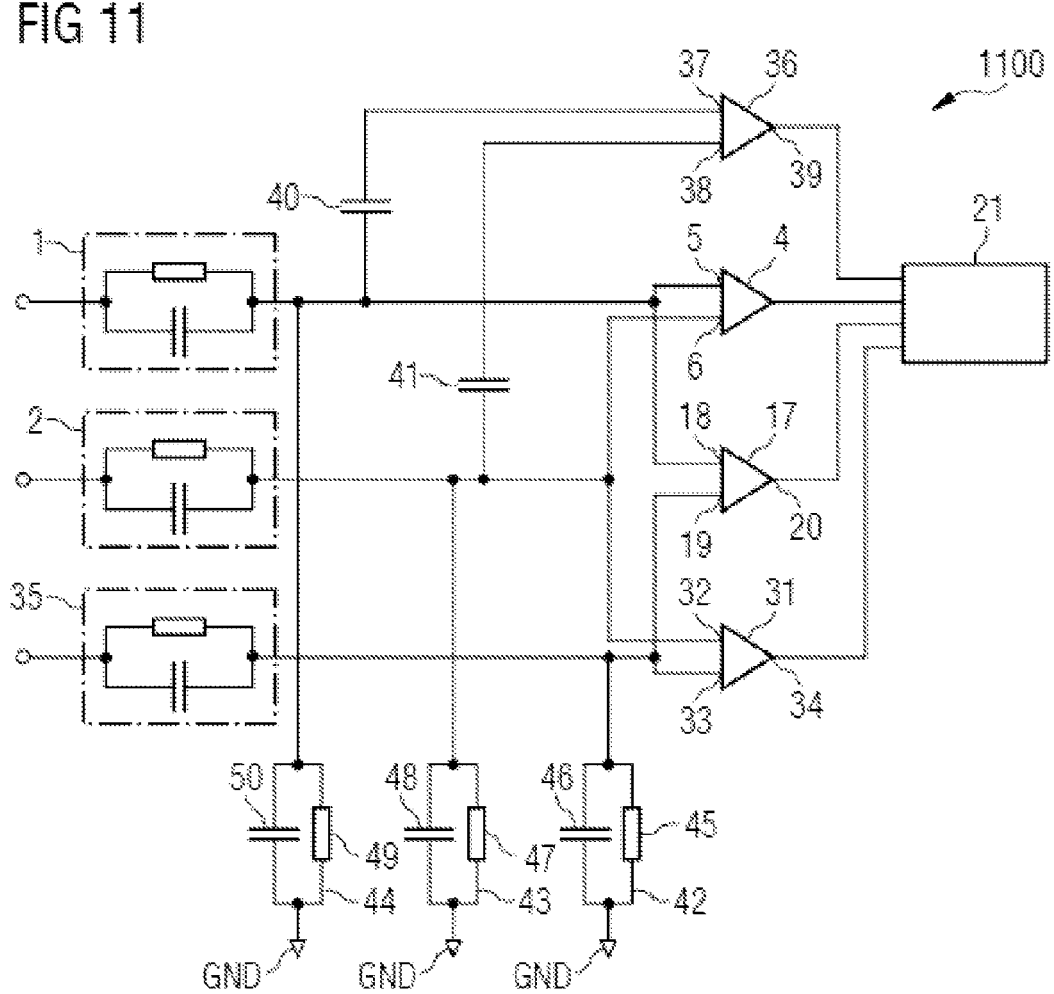
FIG. 11 shows a circuit arrangement with an ESD protective circuit with additional impedances in accordance with one exemplary embodiment.

FIG. 11 shows a measuring circuit 1100 in accordance with one exemplary embodiment. The measuring circuit 1100 may be used to compensate for the interference signals on account of ESD pulses. The measuring circuit has the features shown in FIG. 9. In addition, however, impedances 42, 43, 44 respectively having resistances 45, 47, 49 and capacitances 46, 48, 50 are connected between the individual measurement paths and ground GND. With the aid of the additional impedances 42, 43, 44, the individual measurement paths are balanced, such that the individual measurement paths have identical transfer functions. Even in the event of an ESD pulse occurring, an interference signal brought about by common-mode currents no longer occurs in this arrangement, which is balanced with regard to the impedance. It may suffice even to provide only the measurement path connected to the left foot with an additional impedance and to match the additional impedance to the impedances of the other two measurement paths since the other two measurement paths at best already have an identical transfer function.

Figure 12:
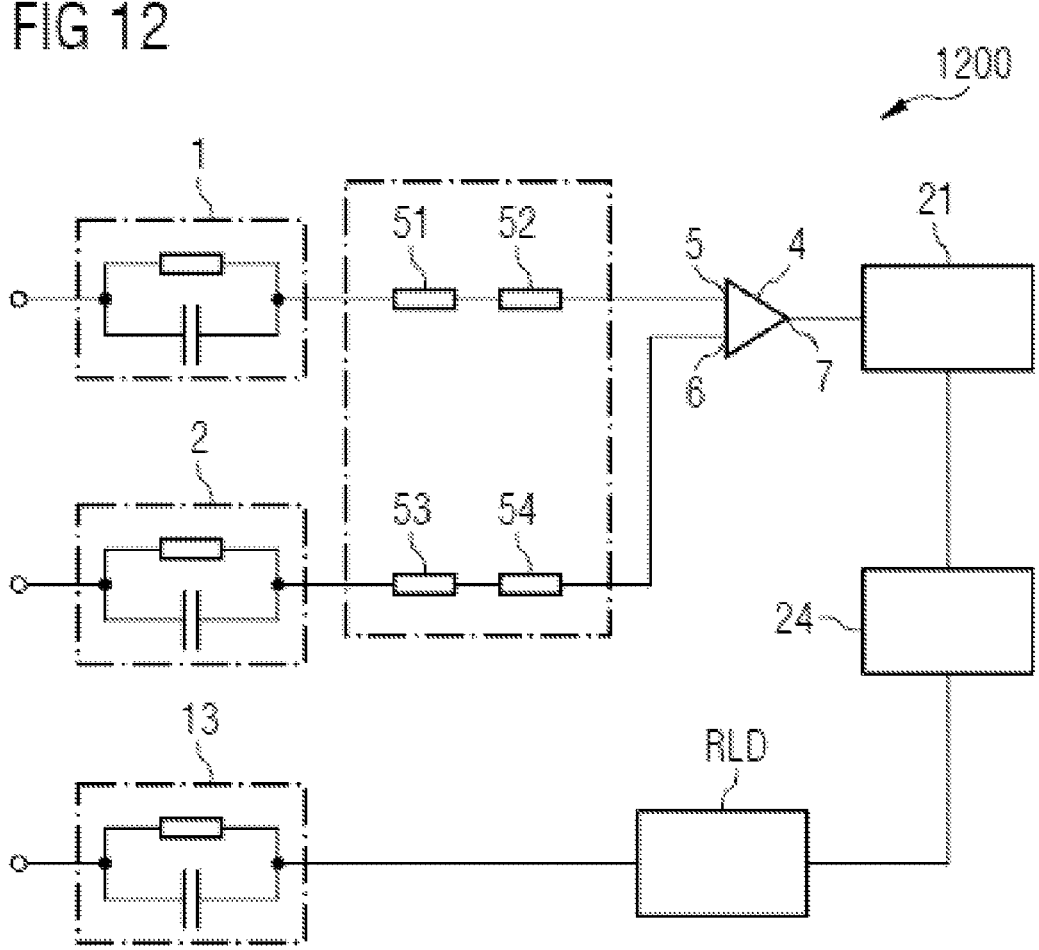
FIG. 12 shows a circuit arrangement with protective resistors that are restricted to the measurement paths in accordance with one exemplary embodiment.

FIG. 12 illustrates a circuit arrangement 1200 for differentially measuring bioelectric signals. The circuit arrangement 1200 is constructed in a similar manner to the circuits shown in FIG. 1 and in FIG. 8.

Like the circuit 800 in FIG. 8, the circuit arrangement 1200 includes, besides a first ECG electrode 1 and a second ECG electrode 2, an amplifier circuit 4 having a first input 5, a second input 6, and an output 7 and also a driver circuit RLD for the right leg. The driver circuit RLD for the right leg drives an additional electrode 13 that is in contact with the right leg of a patient. As already explained in the description of FIG. 8, the additional RLD path serves for applying a reference potential to the body of the patient. In the arrangement shown in FIG. 12, the reference potential is determined based on a differential signal of the signals present at the first and second electrodes 1, 2. The differential signal is detected by a detection unit 21 and communicated to a control unit 24, and is applied to the additional electrode 13 with the aid of the driver circuit RLD.

The arrangement 1200 shown in FIG. 12 includes in each case two protective resistors 51, 52 and respectively 53, 54 on the measurement paths between the first electrode 1 and the first input 5 of the amplifier circuit 4 and between the second electrode 2 and the second input 6 of the amplifier circuit 4. The protective resistors serve to restrict patient auxiliary currents to a predetermined value. Unlike in the case of conventional circuit arrangements, however, the protective resistors are restricted to the measurement paths. In other words, no protective resistors are arranged on the RLD path between the additional electrode 13 and the driver circuit RLD.

The advantage of the arrangement of the protective resistors solely in the measurement paths is that, in this way, the resistance of the RLD path may be minimized, and the current flowing through the RLD path may be maximized, while the current flowing through the measurement path is reduced. This leads to a minimization of interference signals on account of common-mode currents. This may be explained by the fact that the magnitude of the differentially measured common-mode interference voltage given an identical impedance difference is proportional to the current intensity. Compared with the measurement paths, the RLD path has a significantly lower impedance in order to maximize the current through the RLD path in comparison with the currents in the measurement paths and thus to reduce the common-mode interference on the measurement paths. A limitation of the patient auxiliary currents is provided despite the changed arrangement of the protective resistors since the total resistance between two arbitrary poles or electrodes is maintained.

FIG. 13 illustrates a method 1300 for differentially measuring voltages in accordance with one exemplary embodiment. Act 13.I involves detecting a first signal S1 with a first electrode and a second signal S2 with a second electrode. The first electrode and the second electrode are connected to a patient at the input and make available a respective measurement contact at the output. Act 13.II involves determining a differential signal based on the first signal S1 and the second signal S2. Act 13.III involves measuring the current intensity of a common-mode current at a shunt resistor connected to the second electrode 2. Act 13.IV involves determining the transfer function of the measurement paths corresponding to the first electrode 1 and to the second electrode 2. This may be realized, for example, by DC voltage or AC voltage or AC current generation at the two measurement paths and measurements of voltage values generated as a result at the two measurement paths, as are illustrated in FIGS. 6 and 7. Act 13.V involves determining the voltage of a common-mode signal present at the measuring circuit based on the transfer function and the measured common-mode current. Act 13.VI involves calculating a useful signal by subtraction of the differential signal determined in act 13.II and the common-mode signal determined in act 13.V. In this way, even in the event of a correlation between the interference signal and the useful signal, a suppression of the interference signal may be achieved without the intensity of the useful signal itself being impaired.

In comparison with the conventional procedure when minimizing common-mode interference signals, the method according to one or more of the present embodiments is significantly more flexible, more easily handleable, and less time-consuming and laborious for the user.

The method described in detail above and the differential voltage measuring systems illustrated are merely exemplary embodiments that may be modified in a variety of ways by the person skilled in the art without departing from the scope of the invention. The use of the indefinite article "a" and "an" does not rule out the fact that the relevant features may also be present multiply. Likewise, the term "unit" does not rule out the case that the relevant components include a plurality of interacting subcomponents that, if appropriate, may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A differential voltage measuring system comprising:
   two electrodes that are connectable to a patient at an input and make available a respective measurement contact at an output, the two electrodes comprising a first electrode and a second electrode;
   a shunt resistor connected in series with the second electrode;
   first amplifier circuit having a first input for a first signal from the first electrode, a second input for a second signal from the second electrode, and an output;
   a second amplifier circuit having a first input, a second input, and an output, wherein the first input of the second amplifier circuit is connected between the shunt resistor and the second input of the first amplifier circuit, and the second input of the second amplifier circuit is connected between the second electrode and the shunt resistor;
   a first signal detection unit at the output of the first amplifier circuit; and
   a second signal detection unit at the output of the second amplifier circuit, the second signal detection unit configured to detect the signal from the second amplifier circuit as a measurement variable of a current intensity of a common-mode current.

2. The differential voltage measuring system of claim 1, further comprising an adaptive filter between one of the two electrodes and one input of the first input and the second input of the first amplifier circuit, the adaptive filter being set such that the common-mode current is suppressed.

3. The differential voltage measuring system of claim 1, further comprising:
   a first unit and a second unit for DC or AC voltage or current generation at the first input and the second input of the first amplifier circuit; and
   an evaluation unit configured to determine a transfer function of the first electrode and of the second electrode based on voltage values measured at the first input and the second input of the first amplifier circuit.

4. The differential voltage measuring system of claim 3, further comprising a control unit configured to control the first unit and the second unit for DC or AC voltage or current generation at the first input and the second input of the first amplifier circuit, the control unit being configured to drive the first unit and the second unit such that AC current signals having a varying frequency are generated at the first electrode and the second electrode.

5. The differential voltage measuring system of claim 4, wherein the control unit is configured to drive the first unit and the second unit such that AC current signals having an impulse or step-response function are generated at the first electrode and the second electrode.

6. The differential voltage measuring system of claim 3, wherein the evaluation device is configured to determine, based on the detected current intensity of the common-mode current and the determined transfer function, a voltage drop generated by the common-mode current at the shunt resistor and to subtract the voltage drop from the signal detected by the first signal detection unit.

7. The differential voltage measuring system of claim 1, further comprising a plurality of measurement electrodes corresponding to the first electrode, the plurality of measurement electrodes being connected to a patient at an input and making available a respective measurement contact at an output.

8. The differential voltage measuring system of claim 7, further comprising one or more multiplexers connected upstream, the measurement contacts being connectable, by the one or more multiplexers, to the first input and the second input of the first amplifier circuit.

9. The differential voltage measuring system of claim 1, further comprising, for each electrode, a measurement path for measuring common-mode currents, the measurement path being provided with a shunt resistor and being connectable to the respective electrode.

10. The differential voltage measuring system of claim 1, further comprising a further contact for generating a signal at the body of the patient, the signal being regulatable to the common-mode voltage determined at the shunt resistor.

11. The differential voltage measuring system of claim 1, wherein the shunt resistor is arranged in a current path that branches off from a measurement path formed by the second electrode and the second input of the first amplifier at the output of the second electrode, and
   wherein the differential voltage measuring system further comprises a regulatable impedance connected between the shunt resistor and ground.

* * * * *